United States Patent
Bink et al.

(10) Patent No.: US 10,314,757 B2
(45) Date of Patent: *Jun. 11, 2019

(54) INCUBATOR

(71) Applicant: Ningbo David Medical Device Co., Ltd., Ningbo (CN)

(72) Inventors: Jeroen Bink, Breda (NL); Oskar Van Dijk, Breda (NL); Heleen Willemsen, Amsterdam (NL); Jeroen Van Den Hout, Leiden (NL)

(73) Assignee: Ningbo David Medical Device Co., Ltd., Ningbo (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/946,357

(22) Filed: Apr. 5, 2018

(65) Prior Publication Data

US 2018/0221227 A1 Aug. 9, 2018

Related U.S. Application Data

(62) Division of application No. 13/884,826, filed as application No. PCT/NL2010/050762 on Nov. 16, 2010, now Pat. No. 9,968,501.

(51) Int. Cl.
*F24F 13/24* (2006.01)
*A61G 11/00* (2006.01)
(Continued)

(52) U.S. Cl.
CPC ............. *A61G 11/00* (2013.01); *A61M 16/10* (2013.01); *F24F 13/24* (2013.01); *F24F 2013/088* (2013.01)

(58) Field of Classification Search
CPC ...... A61G 11/00; A61G 11/001–11/009; F28F 2009/224; F15D 1/0005
See application file for complete search history.

(56) References Cited

U.S. PATENT DOCUMENTS 2,633,842 A 4/1953 Higgs
3,005,673 A 10/1961 Smith et al.
(Continued)

FOREIGN PATENT DOCUMENTS

EP 0162375 A1 11/1985
EP 0443330 A2 8/1991
(Continued)

OTHER PUBLICATIONS

Nov. 12, 2014—(RU) Office Action—App 2013127287/14—Eng Tran.
(Continued)

*Primary Examiner* — Carrie R Dorna
(74) *Attorney, Agent, or Firm* — Banner & Witcoff, Ltd.

(57) ABSTRACT

An incubator comprises an incubator chamber defined by a bottom part and a top casing covering a bed area of the bottom part. The incubator comprises an air treatment and circulation device for treating air and circulating it through the chamber, said air treatment and circulation device including a ventilator. The air treatment and circulation device is connected to chamber inlet openings which are arranged along one or more sides of said bed area, allowing treated air to flow from the treatment and circulation device into the chamber. The air treatment and circulation device furthermore is connected to at least one chamber outlet opening allowing air to flow out from the chamber to the treatment and circulation device. The air flows in the incubator are routed such that noise is reduced and no high air flow speeds occur near the infant in the incubator.

26 Claims, 2 Drawing Sheets

(51) Int. Cl.
   *A61M 16/10* (2006.01)
   *F24F 13/08* (2006.01)

(56) References Cited

U.S. PATENT DOCUMENTS

| | | |
|---|---|---|
| 4,034,740 A | 7/1977 | Atherton et al. |
| 5,332,872 A | 7/1994 | Ewanek |
| 6,511,414 B1 | 1/2003 | Hamsund |
| RE38,453 E | 3/2004 | Lessard et al. |
| 6,776,710 B1 | 8/2004 | Messmer et al. |
| 2002/0143233 A1 | 10/2002 | Donnelly et al. |
| 2005/0076668 A1 | 4/2005 | Choi |

FOREIGN PATENT DOCUMENTS

| | | |
|---|---|---|
| EP | 1384936 A1 | 1/2004 |
| EP | 1520572 A2 | 4/2005 |
| FR | 2159732 A5 | 6/1973 |
| JP | H10512039 A | 11/1998 |
| WO | 99/21526 A1 | 5/1999 |
| WO | 99/63279 A2 | 12/1999 |
| WO | 0180804 A2 | 11/2001 |

OTHER PUBLICATIONS

Feb. 5, 2015—(EP) Extended Search Report—App 14192302.9.
Apr. 7, 2015—(JP) Notice of Reasons for Rejection—App P2013-538677—Eng Tran.
International Search Report dated Oct. 11, 2011, for PCT/NL2010/050762.
Jun. 10, 2016—U.S. Restriction Requirement—U.S. Appl. No. 13/884,826.
Jan. 11, 2017—U.S. Non-Final Office Action—U.S. Appl. No. 13/884,826.
Jul. 12, 2017—U.S. Final Office Action—U.S. Appl. No. 13/884,826.
Dec. 29, 2017—U.S. Notice of Allowance—U.S. Appl. No. 13/884,826.

INCUBATOR

CROSS-REFERENCE TO RELATED APPLICATIONS

This Application is a Divisional of application Ser. No. 13/884,826 filed on Jul. 24, 2013. Application Ser. No. 13/884,826 is a U.S. National Stage Application, which claims priority to PCT/NL2010/050762, filed Nov. 16, 2010. The entire contents of these applications are incorporated herein by reference in their entirety.

FIELD OF THE INVENTION

The present invention relates to an incubator comprising an incubator chamber defined by a bottom part and a top casing covering a bed area of the bottom part, and comprising an air treatment and circulation device for treating air and circulating it through the chamber, said air treatment and circulation device including a ventilator, wherein the air treatment and circulation device is connected to chamber inlet openings which are arranged along one or more sides of said bed area, allowing treated air to flow from the treatment and circulation device into the chamber, and the air treatment and circulation device furthermore is connected to at least one chamber outlet opening allowing air to flow out from the chamber to the treatment and circulation device.

Such incubators are used in neonatology for intensive care of newborns, possibly prematurely born. Such an incubator is for example known from EP 0162375 A1.

A problem with known incubators is the noise that the ventilator of the air treatment and circulation device makes, which disturbs the infant and which may cause stress and other negative effects on the infants well being and development.

SUMMARY OF THE INVENTION

A first aspect of the present invention has for an object to provide an improved incubator in which the noise generated by the ventilator is reduced.

This object is achieved by an incubator as defined at the outset, wherein the treatment and circulation device has an inlet air duct located between the chamber outlet opening and the ventilator, wherein a baffle unit is arranged in said inlet air duct.

The baffle unit inside the inlet duct, through which air is fed to the ventilator, generates a more homogeneous flow with less turbulence compared to the situation where no baffle unit is present. The low turbulence homogeneous feed flow towards the ventilator causes the ventilator to generate less noise.

In a preferred embodiment a constriction is arranged in the inlet air duct. The constriction removes turbulences from the air flow and increases the flow speed.

More preferably the constriction is arranged between the baffle unit and the ventilator. The constriction which is thus arranged just upstream from the ventilator, results in the air having a favourable angle of attack on the ventilator blades, which reduces air separation on the blades and thereby reduces the noise generated by the ventilator.

In a preferred embodiment the baffle unit comprises a tubular portion which is concentrically arranged in the inlet air duct, such that air can flow along the inner surface as well as the outer surface of the tubular portion. This baffle unit shape generates a particular advantageous homogeneous channel flow with less turbulence.

The baffle unit may advantageously include radial air guiding vanes that extend inwardly from the tubular portion towards the centre axis of the tubular portion and which are preferably are interconnected in the centre of the baffle unit by a centre piece.

The baffle unit and constriction as described here works particularly well with a ventilator of the centrifugal type. However, it must be noted that within the scope of the invention also a baffle unit is conceivable that cooperates with an axial ventilator.

In a particularly preferred embodiment the baffle unit comprises heating elements for heating the air flowing along its surface, wherein the heating elements are preferably incorporated in the tubular portion and/or the air guiding vanes of the baffle unit. The heating elements heat up the baffle unit and thereby allow the air guided along the surfaces of the baffle unit to be heated. The different parts of the baffle unit preferably have a low mass, whereby they are heated in a short time span. Thereby a fast temperature response can be achieved. The location of the baffle unit in the centre of the inlet duct and thus central in the air flow ensures a high heat exchange between the baffle unit and the air flowing along. This results in a short cooling down time span. In all, the structure of the combined baffle and heating unit results in a heating system with a fast system response.

A second aspect of the invention relates to an incubator as defined at the outset, wherein the ventilator of the air treatment and circulation device is arranged in a ventilator chamber and wherein the air treatment and circulation device furthermore has a distribution chamber which is in communication with the ventilator chamber and with the chamber inlet openings. The distribution chamber distributes the air flowing out of the ventilator to the chamber inlet openings and is designed to reduce the air speed.

In a possible embodiment, the distribution chamber is defined by a housing having a substantially flat upper wall and a flat bottom wall extending parallel thereto. This particular of the upper wall and bottom wall prevents that the air flow runs into obstructions during its travel from the ventilator to the chamber inlets.

Preferably, the upper wall and bottom wall have on their longitudinal sides and at least one of their transversal sides an upwardly extending edge portion, wherein the associated edge portions between them define outlet ducts, wherein the free end of the outlet ducts is at least partly open, thereby defining the chamber inlet openings. Preferably, the upwardly extending edge portions are curved. The particular shape of the housing prevents obstacles and tight turns which could create additional pressure losses.

The outlet ducts are closed at their side ends by edge walls interconnecting the upper wall and bottom wall.

In a particularly advantageous embodiment a Venturi hump is arranged at the transition between the ventilator chamber and the distribution chamber. This Venturi hump creates a narrow gap through which the airflow locally accelerates. The created pressure differential over this hump balances the volume flow over the entire width of the Venturi hump such that all chamber inlet openings towards the chamber receive a certain amount of air. This effect is analogue to a water dam in a river which damps out dynamic effects.

Preferably the Venturi hump extends in a curved manner over the bottom wall, preferably in circular manner, thus with a constant radius of curvature. Thereby the air flow over the hump is equally distributed in the directions of the respective outlet ducts and the associated chamber inlets.

In a possible embodiment the ventilator chamber and the distribution chamber and the outlet ducts are defined by one integral casing. In this way a compact and low complex ducting construction can be achieved. No couplings and transition parts are necessary between the different chambers and ducts and therefore a ducting system with a smooth inner surface is provided in which the air flow is disturbed as little as possible.

A third aspect of the invention relates to the routing of the air flows in the incubator chamber. For the comfort of the infant lying in the incubator chamber it is important that the air speeds near the infant are low.

This aspect of the invention has for an object to provide an incubator that is improved or at least provides an alternative with respect to the air flow routing through the incubator chamber.

This object is achieved by an incubator as described at the outset, in which said bed area has a head end and a foot end, two longitudinal sides extending between the head end and the foot end and a transverse side on the head end and a transverse side on the foot end, as well as a centre defined by the intersection of the longitudinal an transversal centre lines, wherein on each of said longitudinal sides one or more of the chamber inlet openings are arranged, wherein the chamber inlet opening(s) on said longitudinal sides are positioned asymmetrically with respect to the centre. The asymmetric arrangement of the chamber inlet openings on the opposing longitudinal ends results in an asymmetric routing of the respective air flows exiting from these inlet openings.

The airflows exiting from the chamber inlet openings at the longitudinal sides, flow along the longitudinal side walls of the casing and along the top. The asymmetric routing prevents collision of the flow in the centre of the chamber top, which has the advantage for keeping both the temperature stability and the required low airspeeds near the infant.

Preferably, the chamber inlet opening(s) on one of the longitudinal sides is/are on the head end half of said longitudinal side and the chamber inlet opening(s) on the opposite longitudinal side is/are on the foot end half of said opposite longitudinal side.

Preferably only on one transversal side one or more chamber inlet openings are arranged, preferably on the foot end. The flow exiting from this inlet at the foot end is relatively weak in order not to disturb the flows originating from the inlets at the longitudinal sides.

In a possible embodiment only one chamber inlet opening is arranged on each of the respective sides, said respective outlet openings preferably having an elongate shape, more preferably being slot shaped. By the slot shaped inlets a wide flow curtain along the walls of the casing is achieved, which shields the interior of the incubator chamber from the temperature influence of the walls.

In a possible embodiment the chamber outlet opening is arranged on the head end.

Preferably, the chamber outlet opening is arranged on a level above the bed area, preferably at least 200 mm above the bed area, more preferably at the half of the height of the chamber. This placement of the outlet opening prevents that the air speeds near the infant lying in the incubator will become too high.

It is noted that the mentioned aspects of the invention can be combined with each other.

EXAMPLES

To better illustrate the apparatus and methods disclosed herein, a non-limiting list of examples is provided here:

1. Incubator comprising an incubator chamber defined by a bottom part and a top casing covering a bed area of the bottom part, and comprising an air treatment and circulation device for treating air and circulating it through the chamber, said air treatment and circulation device including a ventilator, wherein the air treatment and circulation device is connected to chamber inlet openings which are arranged along one or more sides of said bed area, allowing treated air to flow from the treatment and circulation device into the chamber, wherein the air treatment and circulation device furthermore is connected to at least one chamber outlet opening allowing air to flow out from the chamber to the treatment and circulation device, wherein the treatment and circulation device has an inlet air duct located between the chamber outlet opening and the ventilator, and wherein a baffle unit is arranged in said inlet air duct.

2. Incubator according to example 1, wherein in the inlet air duct a constriction is arranged.

3. Incubator according to example 2, wherein the constriction is arranged between the baffle unit and the ventilator.

4. Incubator according to any one of the preceding examples, wherein the baffle unit comprises a tubular portion which is concentrically arranged in the inlet air duct, such that air can flow along the inner surface as well as the outer surface of the tubular portion.

5. Incubator according to example 4, wherein the baffle unit includes radial air guiding vanes that extend inwardly from the tubular portion towards the center axis of the tubular portion.

6. Incubator according to example 5, wherein the radial air guiding vanes are interconnected in the centre of the baffle unit by a centre piece.

7. Incubator according to any one of the preceding examples, wherein the baffle unit comprises heating elements for heating the air flowing along its surface, wherein the heating elements are preferably incorporated in the tubular portion and/or the air guiding vanes of the baffle unit.

8. Incubator according to any one of the preceding examples, wherein said bed area has a head end and a foot end, two longitudinal sides extending between the head end and the foot end and a transverse side on the head end and a transverse side on the foot end, as well as a centre defined by the longitudinal an transversal centre lines, wherein on each of said longitudinal sides one or more of the chamber inlet openings are arranged, wherein the chamber inlet opening(s) on said longitudinal sides are positioned asymmetrically with respect to the centre.

9. Incubator according to any one of the preceding examples, wherein only on one transversal side one or more chamber inlet openings are arranged.

10. Incubator according to any one of the preceding examples, wherein only one chamber inlet opening is arranged on each of the respective sides, said respective inlet openings preferably having an elongate shape, more preferably being slot shaped.

11. Incubator according to example 9, wherein the chamber outlet opening is arranged on the other transversal side.

12. Incubator according to any one of the preceding examples, wherein the chamber outlet opening is arranged on a level above the bed area, preferably at least at the half of the height of the chamber.

13. Incubator according to any one of the preceding examples, wherein the ventilator of the air treatment and circulation device is arranged in a ventilator chamber and wherein the air treatment and circulation device furthermore has a distribution chamber which is in communication with the ventilator chamber and with the chamber inlet openings.

14. Incubator according to example 13, wherein the distribution chamber is defined by a housing having a substantially flat upper wall and a substantially flat bottom wall extending parallel thereto.

15. Incubator according to example 14, wherein the upper wall and bottom wall have on their longitudinal sides and at least one of their transversal sides an upwardly extending edge portion, wherein the associated edge portions between them define outlet ducts.

16. Incubator according to example 15, wherein the free end of the outlet ducts is at least partly open, thereby defining the chamber inlet openings.

17. Incubator according to example 15, wherein the outlet ducts are closed at their side ends by edge walls interconnecting the upper wall and bottom wall.

18. Incubator according to example 15, wherein the upwardly extending edge portions are curved.

19. Incubator according to example 14, wherein at the transition between the ventilator chamber and the distribution chamber a Venturi hump is arranged.

20. Incubator according to example 19, wherein the Venturi hump extends in a curved manner over the bottom wall, preferably with a constant radius of curvature.

21. Incubator according to any of the examples 14-20, wherein the ventilator chamber and the distribution chamber and the outlet ducts are defined by one integral casing.

22. Incubator comprising an incubator chamber defined by a bottom part and a top casing covering a bed area of the bottom part, and comprising an air treatment and circulation device for treating air and circulating it through the chamber, said air treatment and circulation device including a ventilator, wherein the air treatment and circulation device is connected to chamber inlet openings which are arranged along one or more sides of said bed area, allowing treated air to flow from the treatment and circulation device into the chamber, wherein the air treatment and circulation device furthermore is connected to at least one chamber outlet opening allowing air to flow out from the chamber to the treatment and circulation device, wherein the ventilator of the air treatment and circulation device is arranged in a ventilator chamber, and wherein the air treatment and circulation device furthermore has a distribution chamber which is in communication with the ventilator chamber and with the chamber inlet openings.

23. Incubator according to example 22, wherein the distribution chamber is defined by a housing having a substantially flat upper wall and a flat bottom wall extending parallel thereto.

24. Incubator according to example 23, wherein the upper wall and bottom wall have on their longitudinal sides and at least one of their transversal sides an upwardly extending edge portion, wherein the associated edge portions between them define outlet ducts.

25. Incubator according to example 24, wherein the free end of the outlet ducts is at least partly open, thereby defining the chamber inlet openings.

26. Incubator according to example 24, wherein the outlet ducts are closed at their side ends by edge walls interconnecting the upper wall and bottom wall.

27. Incubator according to example 24, wherein the upwardly extending edge portions are curved.

28. Incubator according to example 23, wherein at the transition between the ventilator chamber and the distribution chamber a Venturi hump is arranged.

29. Incubator according to example 28, wherein Venturi hump extends in a curved manner over the bottom wall, preferably with a constant radius of curvature.

30. Incubator according to any of the examples 23-29, wherein the ventilator chamber and the distribution chamber and the outlet ducts are defined by one integral casing.

31. Incubator comprising an incubator chamber defined by a bottom part and a top casing covering a bed area of the bottom part, and comprising an air treatment and circulation device for treating air and circulating it through the chamber, said air treatment and circulation device including a ventilator, wherein the air treatment and circulation device is connected to chamber inlet openings which are arranged along one or more sides of said bed area, allowing treated air to flow from the treatment and circulation device into the chamber, wherein the air treatment and circulation device furthermore is connected to at least one chamber outlet opening allowing air to flow out from the chamber to the treatment and circulation device, wherein said bed area has a head end and a foot end, two longitudinal sides extending between the head end and the foot end and a transverse side on the head end and a transverse side on the foot end, as well as a centre defined by the intersection of the longitudinal an transversal centre lines, wherein on each of said longitudinal sides one or more of the chamber inlet openings are arranged, and wherein the chamber inlet opening(s) on said longitudinal sides are positioned asymmetrically with respect to the centre.

32. Incubator according to example 31, wherein the chamber inlet opening(s) on one of the longitudinal sides is/are on the head end half of said longitudinal side and the chamber inlet opening(s) on the opposite longitudinal side is/are on the foot end half of said opposite longitudinal side.

33. Incubator according to example 31 or 32, wherein only on one transversal side one or more chamber inlet openings are arranged, preferably on the foot end.

34. Incubator according to any one of the examples 31-33, wherein the chamber outlet opening is arranged on the head end.

35. Incubator according to any one of the examples 31-34, wherein only one chamber inlet opening is arranged on each of the respective sides, said respective outlet openings preferably having an elongate shape, more preferably being slot shaped.

36. Incubator according to any one of the examples 31-35, wherein the chamber outlet opening is arranged on a level above the bed area, preferably at least at the half of the height of the chamber.

The invention will be further elucidated in the following detailed description with reference to the drawings.

DETAILED DESCRIPTION

Figure 1:
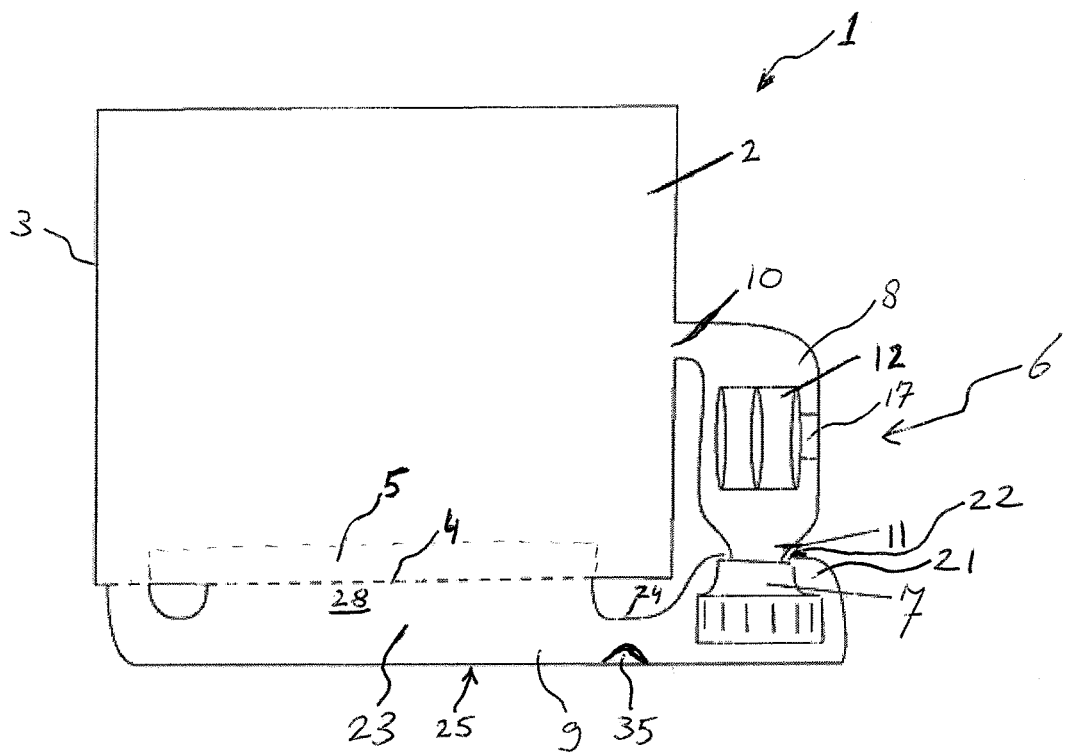
FIG. 1 shows a schematic sectional view of an embodiment of an incubator according to the invention.

In FIG. 1 is shown an incubator 1 for neonatology. The incubator 1 has an incubator chamber 2 which is defined by a casing 3 and a bottom part 4. The bottom part 4 supports a bed portion 5 on which the infant lies.

The incubator 1 furthermore has an air treatment and circulation device 6. The air treatment and circulation device includes a ventilator unit 7, an inlet duct 8 and an outlet ducting assembly 9. The inlet duct may be of tubular shape with for example a substantially circular cross section. The inlet duct 8 is in fluid communication with the incubator chamber 2 through a chamber air outlet 10. The inlet duct 8 is connected at its other end connected with the ventilator unit 7. At this end the inlet duct 8 has a end portion which forms a constriction 11, which means that said end portion of the inlet duct 8 narrows towards the ventilator unit 7.

The ventilator unit 7 comprises a centrifugal ventilator. The air flows towards the centrifugal ventilator in axial direction and exits in a radial direction.

Figure 2:
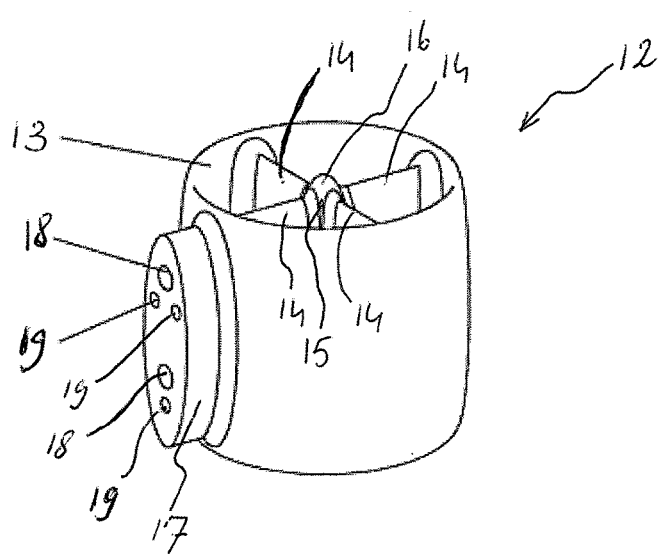
FIG. 2 shows a view in perspective of a baffle unit for the incubator of FIG. 1.

In the inlet duct 8 between the constriction 11 and the chamber outlet opening 10 is arranged a baffle unit 12. The baffle unit 12 is shown in more detail in FIG. 2. The baffle unit 12 has a tubular portion 13. Furthermore the baffling unit 12 has air guiding vanes 14, in this specific embodiment shown, it has four vanes 14 which are attached to the inner side of the tubular portion 13 and extend therefrom radially inwards towards a centre part 15. The vanes 14 are connected to the centre part 15. The centre part 15 has on its end facing the chamber outlet an inlet cone 16.

The cylindrical portion 13 has on its outer side a support 17. The support 17 is in the mounted state (see FIG. 1) attached to the wall of the inlet duct 8.

Preferably, heater elements (not shown) are provided in the cylindrical portion 13 and the radial vanes 14 of the baffle unit 12. The heater elements are connected with external heating components through the connections 18 in the support 17. The baffle unit 12 is attached to the wall of the inlet duct 8 by means of screws that are inserted in the screw holes 19. The support 17 has a sort of vane shape and has only a small contact area with the wall of the inlet duct 8. Thereby heat loss through the support 17 to the wall of inlet duct 8 is reduced. This reduces in use the response time of the heating system. The baffle unit 12 inside the inlet duct 8, through which air is fed to the ventilator unit 7, generates a more homogeneous flow with less turbulence compared to the situation where no baffle unit is present.

The baffle unit 12 and the constriction 11 downstream thereof both condition the air flow in such a way that they both improve each others functionality. A combination of a baffle unit 12 with a constriction 11 is therefore advantageous and it provides a low turbulence homogeneous feed flow towards the ventilator 7, which causes the ventilator 7 to generate less noise. This effect is with the specific configuration of the baffle unit 12 shown in the figures in particular achieved with a centrifugal ventilator.

Figure 4:
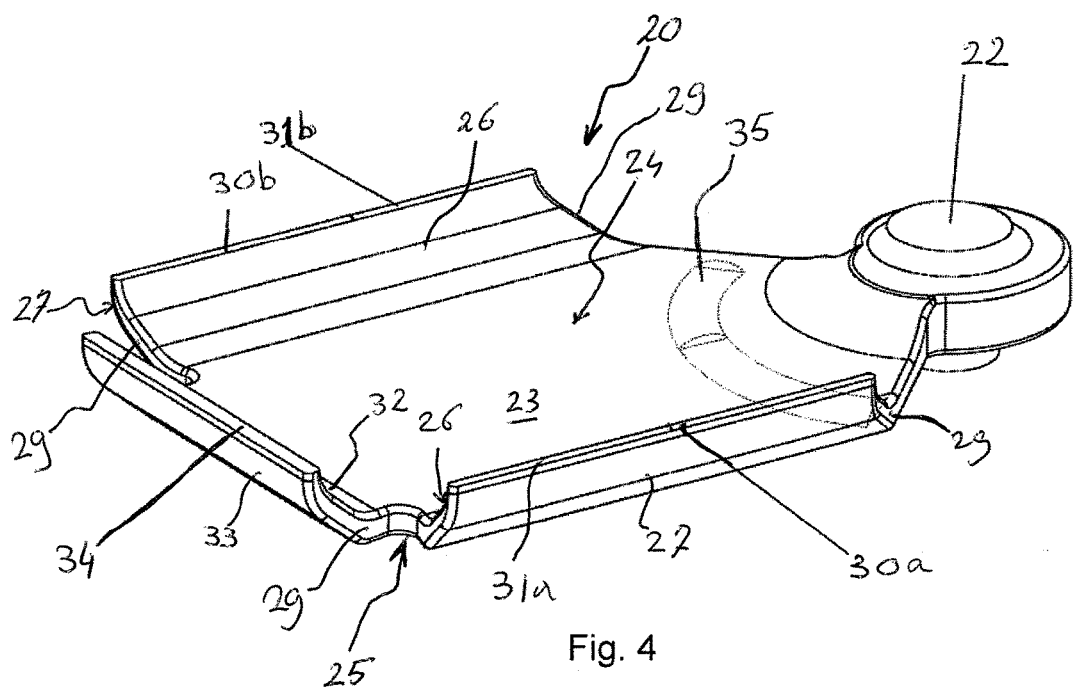
FIG. 4 shows a view in perspective of a housing for the air treatment and circulation device and associated ducting system of the incubator of FIG. 1.

In FIG. 4 is shown a housing 20 for the air treatment and circulation device including its associated ducting system.

The housing 20 defines a ventilator chamber 21 where the ventilator unit 7 is located. The ventilator chamber 21 has an inlet opening 22 through which the ventilator chamber 21 is in fluid communication with the inlet duct 8.

The housing 22 furthermore defines a distribution chamber 23. The housing 20 has a substantially flat upper wall 24 and a flat bottom wall 25 extending parallel thereto which define the upper and bottom wall of the distribution chamber 23. The upper wall 24 and bottom wall 25 respectively have on their longitudinal sides an upwardly extending curved edge portion 26 and 27 respectively. The associated edge portions 26, 27 between them define outlet ducts 28 as can be seen in the sectional view in FIG. 1. The outlet ducts 28 are closed at their side ends by edge walls 29 interconnecting the upper wall 24 and bottom wall 25. The free end of the outlet ducts 28 is partly closed by a wall portion 30a and 30b. The remaining open portion of the free end of the outlet ducts 28 define chamber inlet openings 31a, 31b through which air can flow from the ducting system 9 to the incubator chamber 2.

The ventilator is arranged on the head end side of the incubator. On the transverse side opposite where the ventilator chamber is located the upper wall 24 and bottom wall 25, respectively, have an upwardly extending curved edge portion 32 and 33 respectively. At the free end of these curved wall portions 32, 33 a chamber inlet opening 34 is defined.

At the transition between the ventilator chamber 21 and the distribution chamber 23 a Venturi hump 35 is provided on the bottom wall 25. The Venturi hump 35 extends in a curved, preferably circular arch, shape as is clearly visible in FIG. 4. This Venturi hump 35 creates a narrow gap between the bottom and the top wall through which the airflow locally accelerates. The created pressure differential over this hump 35 balances the volume flow over the entire width of the Venturi hump 35 such that all inlet openings 31a, 31b, 34 towards the incubator chamber 2 receive a certain amount of air. This effect is analogue to a water dam in a river which damps out dynamic effects. Without this measure the dynamics added to the flow by the ventilator 7 will cause most air exiting through opening 34, and almost none through openings 31a, 31b.

Figure 3:
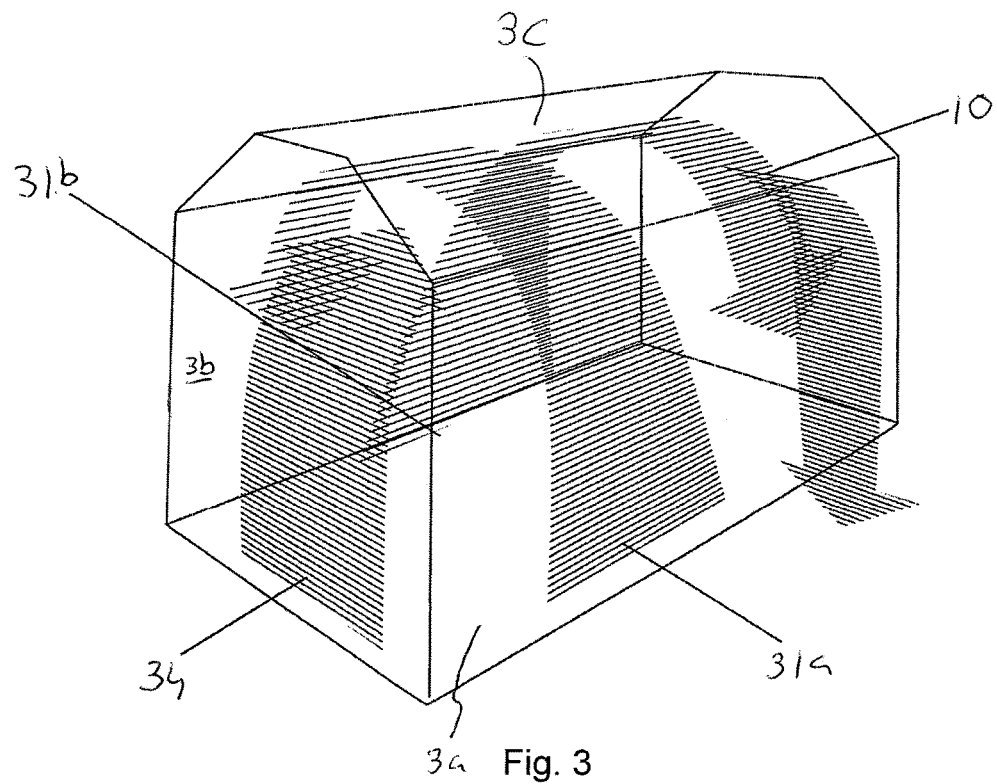
FIG. 3 shows a schematic view in perspective of the incubator chamber of the incubator of FIG. 1, in which the air flows are indicated.

In FIG. 3 is shown how the air flows are directed through the incubator chamber 2. The inlets 31a, 31b and 34 and the outlet 10 are schematically indicated.

The airflows exiting from the chamber inlet openings 31a and 31b at the longitudinal sides, flow upwardly along the longitudinal side walls 3a and 3b of the casing 3 and along the top 3c. The asymmetric routing prevents collision of the flow in the centre of the chamber top 3c, which is an advantage for keeping both the temperature stability and the required low airspeeds near the infant. The flow exiting from the inlet 34 is relatively weak in order not to disturb the flows originating from the inlets 31a, 31b at the longitudinal sides.

The invention claimed is:

1. An incubator comprising an incubator chamber defined by a bottom part and a top casing covering a bed area of the bottom part, and comprising an air treatment and circulation device for treating air and circulating air through the incubator chamber, said air treatment and circulation device including a ventilator;

wherein the air treatment and circulation device is connected to at least one chamber inlet opening which is arranged along one or more sides of said bed area, allowing treated air to flow from the treatment and circulation device into the incubator chamber;

wherein the air treatment and circulation device is furthermore connected to at least one chamber outlet opening allowing air to flow out from the incubator chamber to the treatment and circulation device;

wherein the treatment and circulation device has an inlet air duct located between the at least one chamber outlet opening and the ventilator;

wherein a baffle unit is arranged in said inlet air duct;

wherein the ventilator of the air treatment and circulation device is arranged in a ventilator chamber and wherein the air treatment and circulation device furthermore has a distribution chamber which is in communication with the ventilator chamber and with said at least one chamber inlet opening; and wherein a Venturi hump is arranged at a transition between the ventilator chamber and the distribution chamber.

2. The incubator according to claim 1, wherein a constriction is arranged in the inlet air duct.

3. The incubator according to claim 2, wherein the constriction is arranged in the inlet air duct between the baffle unit and the ventilator.

4. The incubator according to claim 1, wherein the baffle unit comprises heater elements incorporated in the baffle unit to heat up the baffle unit for heating the air flowing along a surface of the baffle unit.

5. The incubator according to claim 1, wherein the distribution chamber is defined by a housing having a substantially flat upper wall and a substantially flat bottom wall extending parallel to said upper wall.

6. The incubator according to claim 5, wherein the upper wall and bottom wall have on their longitudinal sides and at least one of their transversal sides an upwardly extending edge portion, wherein at least one outlet duct is defined between said upwardly extending edge portions.

7. The incubator according to claim 6, wherein a free end of said at least one outlet duct is at least partly open, thereby defining said at least one chamber inlet opening.

8. The incubator according to claim 6, wherein said at least one outlet duct is closed at its side end by edge walls interconnecting the upper wall and the bottom wall.

9. The incubator according to claim 6, wherein said upwardly extending edge portions are curved.

10. The incubator according to claim 6, wherein the ventilator chamber, the distribution chamber and said at least one outlet duct are defined by one integral casing.

11. The incubator according to claim 5, wherein the Venturi hump extends in a curved manner over the bottom wall.

12. The incubator according to claim 5, wherein the Venturi hump extends in a curved manner over the bottom wall with a constant radius of curvature.

13. An incubator comprising an incubator chamber defined by a bottom part and a top casing covering a bed area of the bottom part, and comprising an air treatment and circulation device for treating air and circulating air through the incubator chamber, said air treatment and circulation device including a ventilator;
    wherein the air treatment and circulation device is connected to at least one chamber inlet opening which is arranged along one or more sides of said bed area, allowing treated air to flow from the treatment and circulation device into the incubator chamber;
    wherein the air treatment and circulation device is furthermore connected to at least one chamber outlet opening allowing air to flow out from the incubator chamber to the treatment and circulation device;
    wherein the ventilator of the air treatment and circulation device is arranged in a ventilator chamber;
    wherein the air treatment and circulation device furthermore has a distribution chamber which is in communication with the ventilator chamber and with said at least one chamber inlet opening; and
    wherein a Venturi hump is arranged at a transition between the ventilator chamber and the distribution chamber.

14. The incubator according to claim 13, wherein the distribution chamber is defined by a housing having a substantially flat upper wall and a flat bottom wall extending parallel to said upper wall.

15. The incubator according to claim 14, wherein the upper wall and bottom wall have on their longitudinal sides and at least one of their transversal sides an upwardly extending edge portion, wherein at least one outlet duct is defined between said upwardly extending edge portions.

16. The incubator according to claim 15, wherein a free end of said at least one outlet duct is at least partly open, thereby defining said at least one chamber inlet opening.

17. The incubator according to claim 15, wherein said at least one outlet duct is closed at its side end by edge walls interconnecting the upper wall and bottom wall.

18. The incubator according to claim 17, wherein said upwardly extending edge portions are curved.

19. The incubator according to claim 15, wherein the ventilator chamber, the distribution chamber and said at least one outlet duct are defined by one integral casing.

20. The incubator according to claim 14, wherein the Venturi hump extends in a curved manner over the bottom wall.

21. The incubator according to claim 14, wherein the Venturi hump extends in a curved manner over the bottom wall with a constant radius of curvature.

22. An incubator comprising an incubator chamber defined by a bottom part and a top casing covering a bed area of the bottom part, and comprising an air treatment and circulation device for treating air and circulating air through the incubator chamber, said air treatment and circulation device including a ventilator;
    wherein the air treatment and circulation device is connected to at least one chamber inlet opening which is arranged along one or more sides of said bed area, allowing treated air to flow from the treatment and circulation device into the incubator chamber;
    wherein the air treatment and circulation device is furthermore connected to at least one chamber outlet opening allowing air to flow out from the incubator chamber to the treatment and circulation device;
    wherein the treatment and circulation device has an inlet air duct located between the chamber outlet opening and the ventilator;
    wherein a baffle unit is arranged in said inlet air duct; and
    wherein the baffle unit comprises a tubular portion which is concentrically arranged in the inlet air duct, such that air flows along an inner surface as well as an outer surface of the tubular portion.

23. The incubator according to claim 22, wherein heater elements are incorporated in the tubular portion to heat up the baffle unit for heating air flowing along surfaces of the baffle unit.

24. The incubator according to claim 22, wherein the baffle unit includes radial air guiding vanes that extend inwardly from the tubular portion towards a center axis of the tubular portion.

25. The incubator according to claim 24, wherein said radial air guiding vanes are interconnected in the center of the baffle unit by a center piece.

26. The incubator according to claim 24, wherein heater elements are incorporated in said radial air guiding vanes of the baffle unit to heat up the baffle unit for heating air flowing along surfaces of the baffle unit.

* * * * *